(12) United States Patent
Gruber et al.

(10) Patent No.: US 7,985,190 B2
(45) Date of Patent: Jul. 26, 2011

(54) NON-INVASIVE SKIN CONTOURING DEVICE TO DELAMINATE SKIN LAYERS USING TISSUE RESONANCE

(76) Inventors: William H. Gruber, Southborough, MA (US); Paul Westhaver, Newburyport, MA (US)

(*) Notice: Subject to any disclaimer, the term of this patent is extended or adjusted under 35 U.S.C. 154(b) by 864 days.

(21) Appl. No.: 11/403,074

(22) Filed: Apr. 12, 2006

(65) Prior Publication Data
US 2006/0241531 A1 Oct. 26, 2006

Related U.S. Application Data

(60) Provisional application No. 60/670,529, filed on Apr. 12, 2005.

(51) Int. Cl.
*A61H 1/00* (2006.01)
(52) U.S. Cl. .............................. 601/46; 601/2

(58) Field of Classification Search .................. 601/46, 601/2–4, 48, 67–73, 78–83; 604/22
See application file for complete search history.

(56) References Cited

U.S. PATENT DOCUMENTS

| 4,549,535 | A * | 10/1985 | Wing .............................. 601/108 |
| 6,322,532 | B1 * | 11/2001 | D'Sa et al. ....................... 604/22 |
| 6,443,914 | B1 * | 9/2002 | Costantino ........................ 601/2 |
| 7,468,046 | B2 * | 12/2008 | Takashima ....................... 601/46 |
| 2002/0120225 | A1 * | 8/2002 | McDaniel ......................... 604/22 |
| 2005/0049535 | A1 * | 3/2005 | Reinmuller ...................... 601/160 |
| 2005/0049546 | A1 * | 3/2005 | Messerly et al. ................. 604/22 |
| 2006/0094988 | A1 * | 5/2006 | Tosaya et al. ..................... 601/2 |

* cited by examiner

*Primary Examiner* — Justine R Yu
*Assistant Examiner* — Valerie Skorupa
(74) *Attorney, Agent, or Firm* — Kriegsman & Kriegsman

(57) ABSTRACT

A system and method for treating cellulite tissue and related conditions comprising apparatus configured to transmit shear and other vibration modes beneath a patient's skin sufficient to break down connective tissue so that pocketing and dimpling of adjacent skin is ameliorated.

8 Claims, 5 Drawing Sheets

NON-INVASIVE SKIN CONTOURING DEVICE TO DELAMINATE SKIN LAYERS USING TISSUE RESONANCE

CROSS REFERENCE TO RELATED APPLICATIONS

This application claims benefit of priority from U.S. Provisional Patent Application No. 60/670,529, filed Apr. 12, 2005, which is incorporated herein by reference as though set forth in its entirety.

FIELD OF THE INVENTION

The invention relates to methodologies to treat unsightly skin topography and appearance. It further relates to use of ultrasound to treat skin conditions. Most particularly, it relates to the treatment with ultrasound of the skin condition known as cellulite.

BACKGROUND OF THE INVENTION

Skin irregularities are commonly treated by physical manipulation of the surface and the underlying tissue of the skin. For example, it is believed and therefore practiced that massage therapy reduces the pocketing and wrinkling of the surface texture of the skin.

In actuality, this belief is partly well founded but the result is not only temporary but also short lived. The short life of improvement is due to the fact that improvement is caused by edema. Acute response to physical agitation of skin is often manifested as edema, which is localized swelling that inflates the tissues of the skin and yields a temporary skin smoothing. This acute tissue response abates in a short period of time. However, perception of massage-type therapies is positive because of the legitimate immediate and visible results that the massage recipient witnesses.

One of the most common irregularities in the surface of the skin, predominantly in women, is what is referred to popularly as cellulite. Cellulite is the dimpling and pocketing of the skin and in the skin, particularly in the buttocks and posterior upper thighs.

The morphology of the tissue that causes the pocketing and dimpling of skin in cellulite was long believed to be accumulation of fat tissue under the skin. Consequently many treatments have been developed that reduce the fat content beneath the surface of the skin. These treatments reduce fat volume and the general contour of the skin but do not address the specific underlying causes of the dimpling.

For example, one of the leading treatments for cellulite reduction today is surgical liposuction. Liposuction is effective in reducing fat volume but often aggravates the dimpling and actually sometimes reduces the visual appeal of the surface of the skin. In fact, this leading treatment, widely thought to ameliorate cellulite, actually aggravates skin dimpling.

The underlying cause of the dimpling of the skin is localized inflation of the fat cells with the coincident contraction of the connective tissue distributed amidst and surrounding the fat cells. The dimpling is an aggregate response to a distributed cellular-level tensegrity field. (Tensegrity is to be understood as a characteristic property of a stable three-dimensional structure consisting of members under tension that are contiguous and members under compression that are separated by the former.) In the cellulite condition, cell membranes and connective tissue shrink relative to adjacent fat cells. In summary, the manifestation known as cellulite is not a bulging of fat outward but a tugging of connective tissue inward in localized areas. The connective tissue that causes the contractions is located about 1-2 mm below the surface of the skin.

Methods to treat the tissue below the skin without affecting the surface of the skin have been developed. One such technology is High Frequency Focused Ultrasound (HFFU). HFFU attempts to induce a stress field below the surface of the skin while simultaneously preventing injury to the skin surface. HFFU utilizes a geometric low energy acoustic field projected through tissue and a medium that is focused at a point or line below the surface of the skin. The physical shape of the projector or the phasing of elements of the projector array provides the required stress field direction and amplification. In this technology, resonance is not employed. The effect is highly localized, but it often projects energy too deep into the tissue to provoke a useful tissue response.

It is therefore an object of this invention to provide an improved method of treating the true condition that underlies cellulite. It is a further object of the invention to provide a method of using ultrasound that reliably improves the condition of subcutaneous tissue, thereby alleviating or eliminating the cellulite condition. It is yet a further object of this invention to accomplish improvement of the cellulite condition by providing a resonant ultrasound field.

SUMMARY OF THE INVENTION

The device of the current invention establishes a dynamic condition in the skin layer and in the fat layer below such as to cause the skin to dislocate from the underlying connective tissues, whereby the upper layers of skin are conditioned for healing in a controlled fashion. The healing of the affected tissue removes unsightly topography and discoloration. The device utilizes a standing wave to both target the position of the stress field in the tissue and to generate the amplitudes of the stress condition in relation to the surrounding tissue.

The device consists of a plurality of components well known in the art, which, when assembled and operated in a coordinated fashion in proximity to tissue of specific character, produce a resonance condition below the skin. The resonance condition is a specific dynamic condition which establishes a standing wave in the dermis such that there are portions in the dermis under the influence of the device that move harmoniously with the device, others that move in opposition to the device, and still others that do not move at all. Coincidental with the standing wave of motion is a standing wave of stress in the tissue. The standing stress wave yields positions in the tissue that are under no stress and positions in the tissue that are under stress and still other positions in the tissue that are under stress in alternate sense to other positions in the tissue.

The device is configured so that the standing wave is maintained at such intensity and duration as to cause the structural integrity of the connective tissue to fail. The standing stress wave permits the targeting of the stress field within the subcutaneous layers of the dermis and adjacent fat layers so that the surface of the skin and particular regions beneath the skin remains without trauma. The target areas where the tissue failure occurs is adjusted by the design of the specific resonance modes and frequencies of the device.

The invention features the external imposition of a resonant vibration field just below the skin such that a standing-wave type of stress field is created at a region below the surface of the skin sufficient to cause a histological response below the skin without causing trauma to the surface of the skin. An energy source establishes a resonant vibrational displacement field on the surface of the body and is controlled by feedback to establish a sub-surface resonant stress field. The stress field causes the relevant connective tissue to go to mechanical yield or even failure. Causing such yield triggers a healing response in the connective tissue that causes cellulite. The therapy can optionally be used in combination with any other treatment technique or apparatus.

BRIEF DESCRIPTION OF THE DRAWINGS

The invention can be more fully understood by referring to the following detailed description taken in conjunction with the accompanying drawings, in which.

DETAILED DESCRIPTION OF THE PREFERRED EMBODIMENT

Figure 1A:
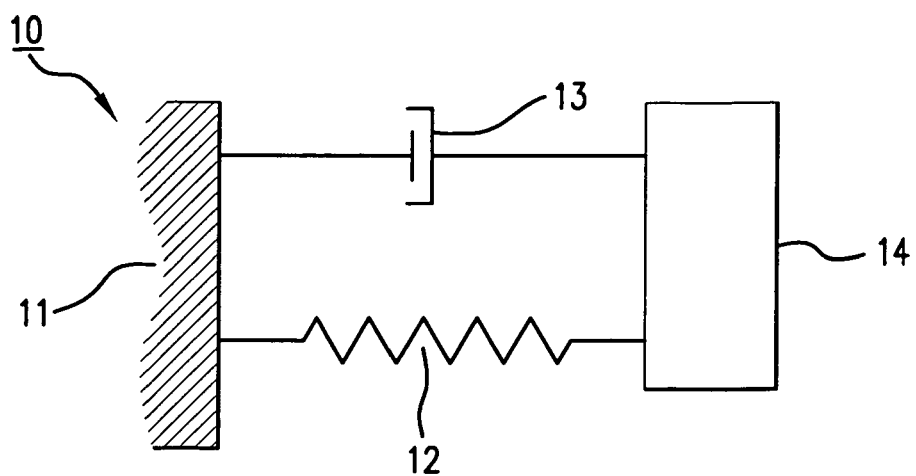
FIG. 1 portrays the mechanical phenomenon of resonance.

In general, skin and the tissue adjacent to it behave mechanically as a composite material. The general response of mechanical systems to vibration is described by the well known relationship of damped vibration. The fumdamental mechanical nature of that response is shown in FIG. 1A, showing a transducer 11 transmitting a driving vibration force $F \sin(\omega)$ into the system. The schematic system comprises an elastic "spring" component 12 having a spring constant K, a mass M 14, and a damping component (sometimes referred to as a dashpot) 13 having a damping coefficient C. The response of the system is determined from the well known differential equation $M\, d^2x/dt^2 + C\, dx/dt + Kx = F \sin(\omega)$.

Figure 1B:
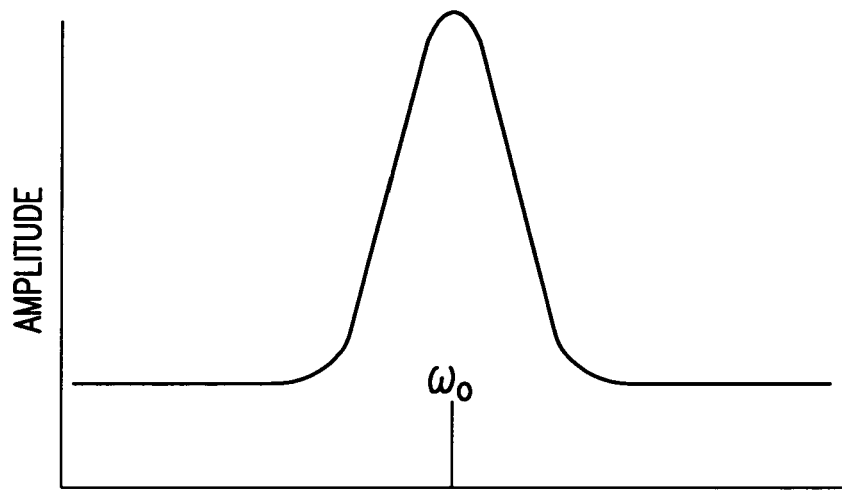
Figure 1C:
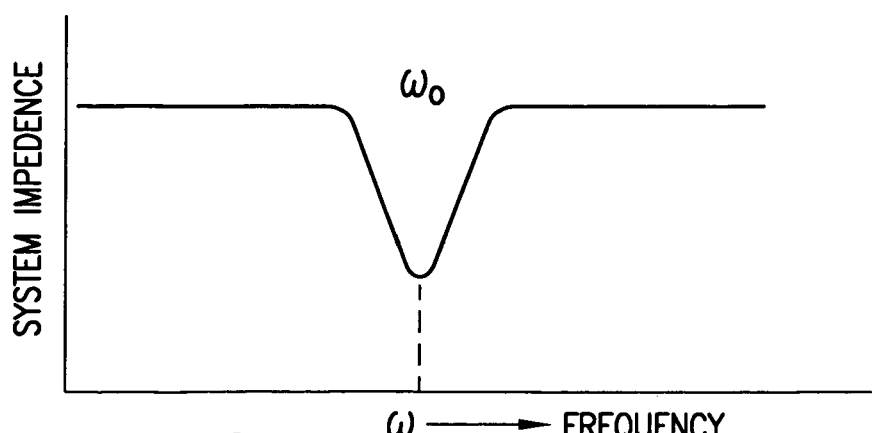

The response of such a system as a function of frequency is shown in FIG. 1B. The figure portrays the well known phenomenon of mechanical resonance, in which the amplitude of displacement is a maximum at a characteristic frequency of the system known as the resonant frequency, denoted here as $\omega_0$. The feature of this phenomenon that the current invention takes advantage of is shown in FIG. 1C. As this figure shows, the system impedance in response to a forcing vibration is a minimum at the resonant frequency.

Figure 2A:
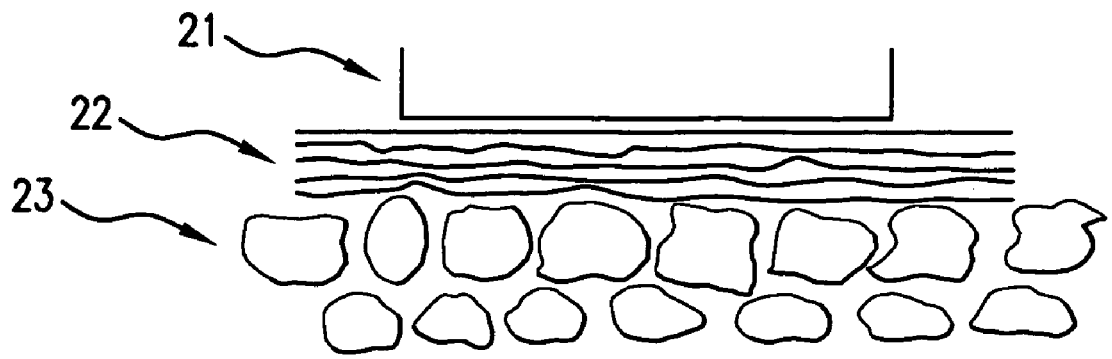
FIG. 2 shows properties of the phenomenon of mechanical resonance in skin and adjacent tissue.
Figure 2B:
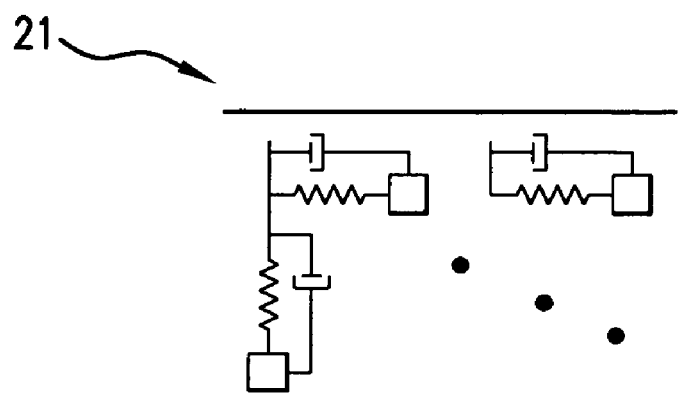
Figure 2C:
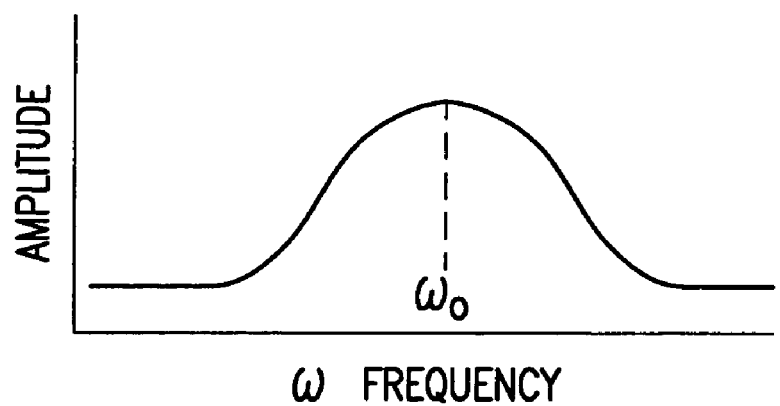

As FIGS. 2A, 2B, and 2C show, the behavior of tissue is more complicated than the simple system portrayed in FIG. 1, but it exhibits very similar properties. FIG. 2A is a schematic of a cross section of skin and tissue beneath the skin with a vibration transducer 21 in contact with the skin. The transducer 21 is mechanically connected to the epidermis and dermis 22 by an adhesive layer (not shown). Beneath the dermis 22 is a layer of cells 23 partly comprising fat cells and partly comprising interstitial connective tissue. As shown in FIG. 2B, the mechanical behavior of the tissue is that of a composite material having distributed properties that can be modeled as a large three dimensional matrix of damped resonators each comprising a mass, a dashpot, and a spring.

The overall behavior of such a distributed system is shown in FIG. 2C. The distributed system modeling the mechanical response of tissue again exhibits resonant behavior, perhaps with a wider peak around the resonant frequency. Nonetheless there is a resonant frequency $\omega_0$ at which amplitude peaks and system impedance dips. The general behavior of tissue near the skin is in accordance with this analysis.

A prototype system comprising a vibration transducer, adhesive for removably attaching the vibration transducer to the skin so that vibration could be reliably transmitted to the skin and thence to underlying tissue, a vibration driver, and a control system for varying the frequency and intensity of vibration was used for proof of concept testing. In this testing various modes of shear vibration were used, including one and two dimensional linear shear and orbital shear motion, but it is to be understood that the invention is not limited to shear modes of vibration but includes use of all other physically possible modes as well.

As the control system increased the frequency and power of the system, a resonant state was achieved in which standing surface waves were seen on the skin. It was inferred that a very similar resonant state was taking place underneath the skin. As the power and frequency of oscillation increased above the resonance point, the indication of resonant behavior receded and gradually ceased. When the direction of frequency variation was gradually reduced, the skin and underlying tissue again passed through resonance. Resonance can alternately be determined by observation of surface waves on the skin, by a drop in the current required to drive the vibration source, or by any other method known to those skilled in the art.

The vibration at resonance induced mild disruption to tissue beneath the skin sufficient to produce welts. These welts later healed so that the skin resumed its normal appearance.

Figure 3:
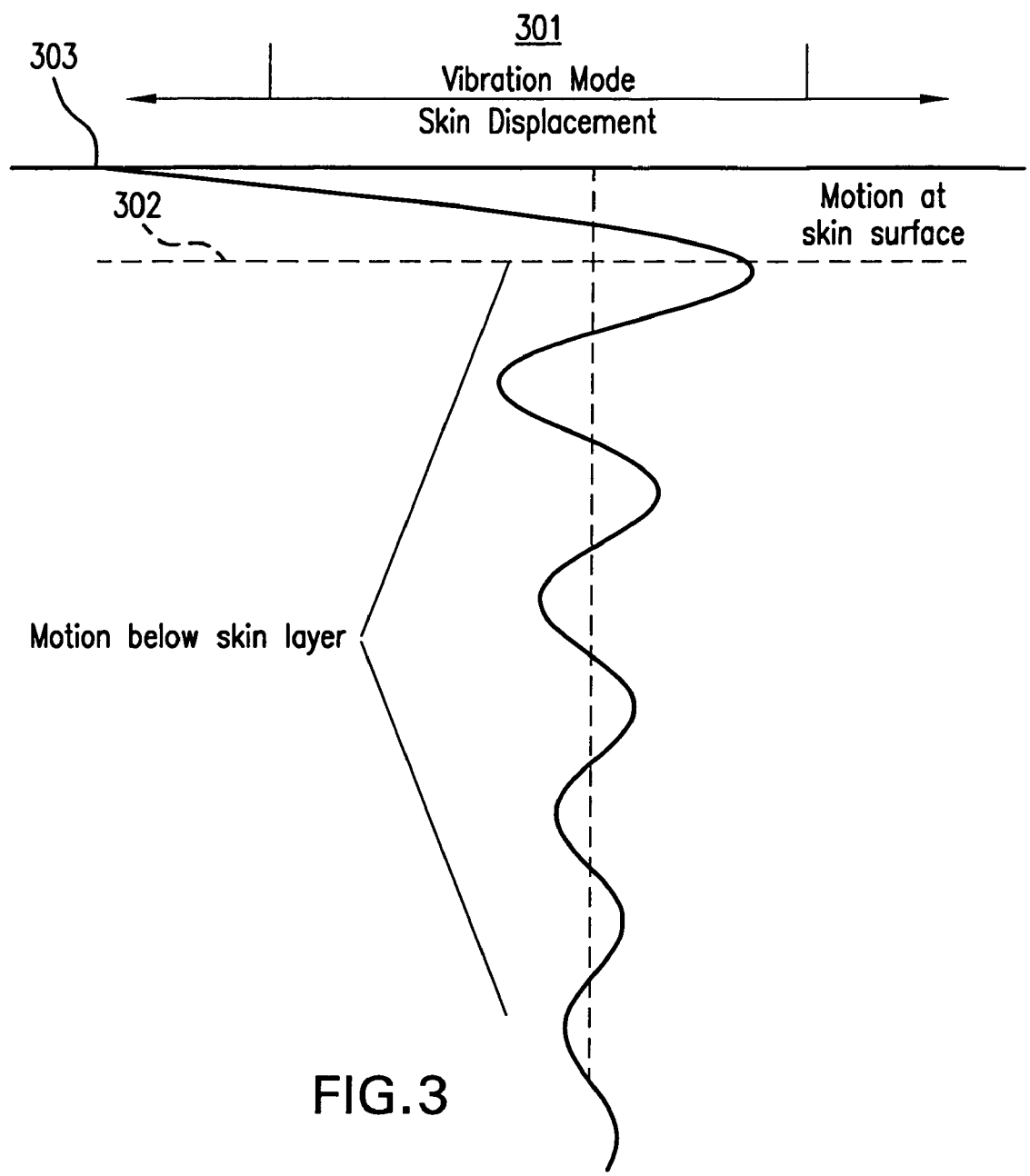
FIG. 3 illustrates an overall schematic view of a resonant stress field system, in relation to the displacement of tissue at resonance in one embodiment.

The operation of this invention with respect to alleviating cellulite conditions can be understood as follows. (In this discussion, the vibration transducer, the vibration source, and the coupling adhesive are referred to for convenience as the device effecter.) FIG. 3 shows the general physical relationship between a device effecter and the skin. The effecter 301 is applied to the skin in such a fashion as to prevent motion between the effecter and the skin surface 302. An adhesive layer 303 can appropriately be used to accomplish limited motion between the effecter 301 and the skin 302.

Figure 4:
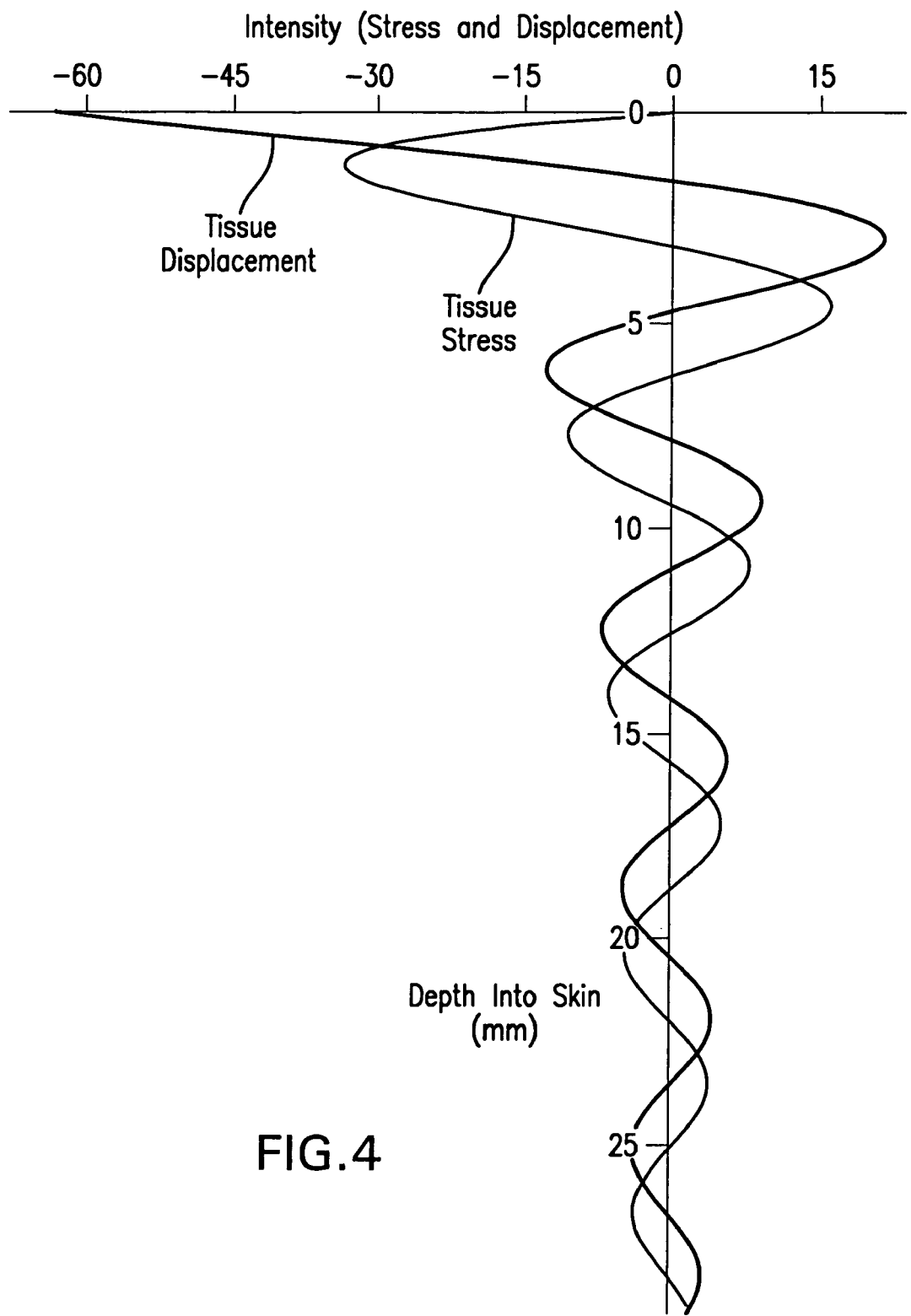
FIG. 4 illustrates an overall schematic view of a resonant stress field system, indicating the standing dynamic displacement field in relation to the skin surface and one embodiment of the motion in the tissue.

FIG. 4 portrays the state of displacement of the tissue that is in force-contact with an excitation surface. The wave, stimulated on the surface, is conducted by the tissue into the depths of the tissue beneath the surface. The vibration energy may be of any direction or superposition of directions. It may be of any frequency of complexity of frequencies that is physically compatible with the mechanical properties of the tissue of interest. The vibration may be of any mode or complexity of modes. The device uses the resulting motion and stress due to motion, in its complexity of modes and phases to establish a stress field in the exact layer of tissue to cause the desired failure of the structure of the tissue in the position desired.

The design of the device enables coupling the device to the tissue of the patient and thereby transmiting vibration energy to the tissue. The vibration energy is dissipated in the tissue through normal loss mechanisms and heat. However, in the vibration condition of resonance the losses are insufficient to dampen motion. The motion is additive to such an extent that large relative motions are generated in a small depth of tissue with low energy input.

Figure 5:
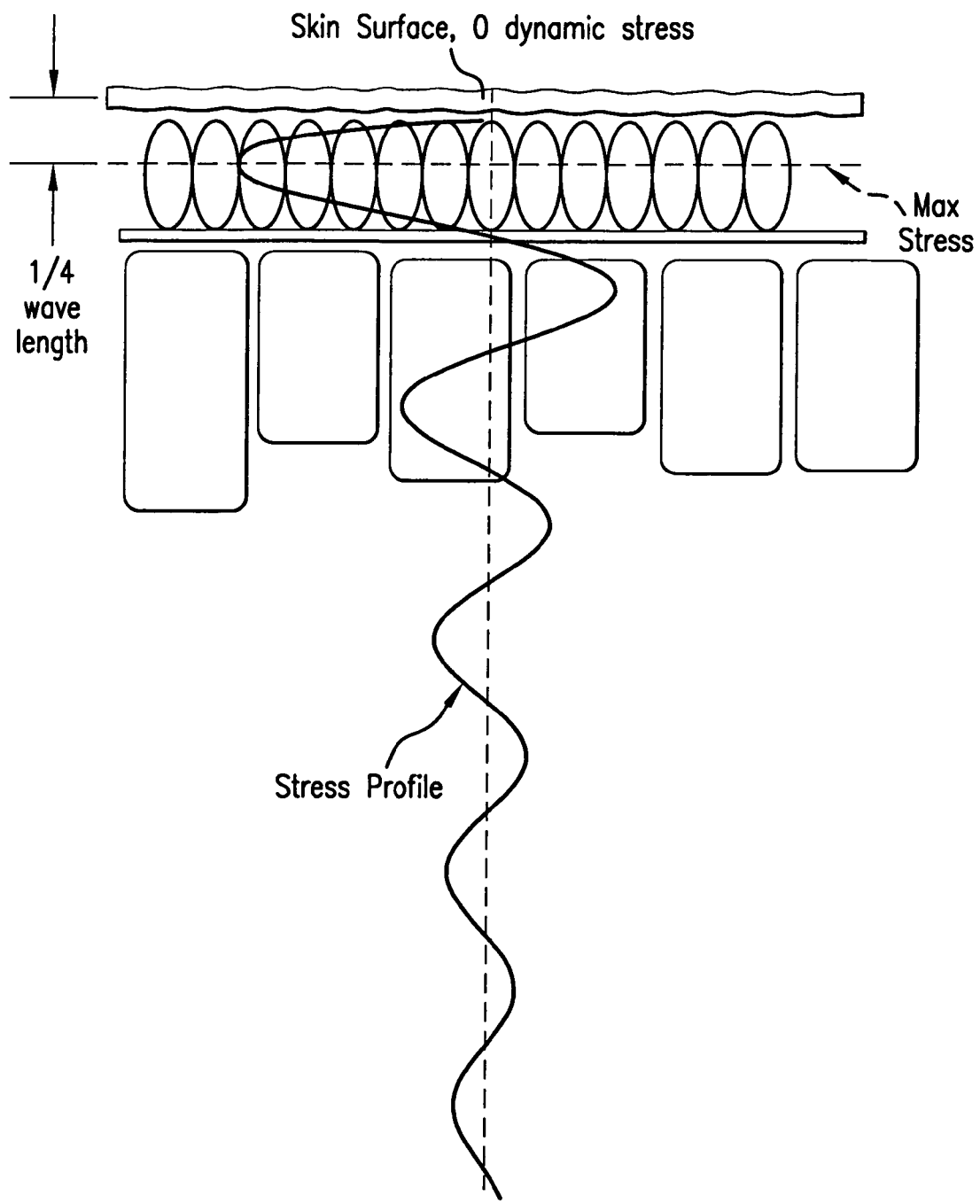
FIG. 5 illustrates an overall schematic view of a resonant stress field system, indicating the standing dynamic stress field in the tissue.

FIG. 5 illustrates the state of stress in the tissue as a consequence of the resonant displacement field. Force flow from the effecter to the skin can be accomplished by a gas column, fluid column, or a solid material. Each of the materials possesses a variety of possible damping and coupling possibilities, any of which would be appropriate for a variety of clinical applications.

The purpose of the coupling of the effecter 301 to the skin is to induce a complex vibration field in the skin. The vibration field induced into the skin may exist in any physically reasonable range of frequencies. The vibration field in this invention is unique in its establishment of a resonant vibration field within the skin. The coupling of the effecter to the skin can be achieved in a number of ways, depending in part on the mode of vibration being used for therapy. In particular, coupling can be through use of an adhesive or alternatively using fluid, pressurized fluid, gas or pressurized gas, or simply frictional contact.

With the application of a resonant vibration field within the skin tissue, as shown in FIG. 5, the stress field in the skin is out of phase with the displacement field by 90 degrees. This is considered to be a resonance. The creation of a standing damped vibration field in the skin tissue permits high stress in the tissue with the application of low energy at the surface of the skin.

In addition, the wave form of the resonant vibration field facilitates zones of zero stress in the tissue, and zones of very high stress in close proximity to one another, separated by repeatable, predictable periods dictated by the resonant wave mechanics of the tissue. By creating a particular frequency or frequencies and mode(s) of vibration the high stress field can be placed with some precision below the surface of the skin. This is quite different from focusing a collected vibration field at a point or line beneath the skin. Focused ultrasound utilized the geometry of the emitter to yield stress amplification. High Frequency Focused Ultrasound yields energies at the surface of the skin below the threshold that causes damage to the skin. The power density is raised by simple geometry to tissue destruction levels by focusing below the surface of the skin similar to a magnifying glass.

Resonant vibration requires no such focusing. The stationary stress field is existent as a function of a standing resonant wave in the tissue. The location of the stress field is ¼ wavelength below the surface of the skin based on the displacement waveform. In addition, other high stress layers exist at ½ wave intervals deeper into the tissue but at progressively lower intensities because of viscous damping in the tissue.

The resonant stress field below the surface of the skin exists in the connective tissue causing, in time, partial or total destruction of the connective tissue, releasing the puckering, and prompting a healing response. The resonant stress field does not exist at any other planes in the tissue other than the planes targeted.

A plurality of vibrations can be superimposed to yield a net resonant stress condition in the tissue that best suits the geometry of the clinical situation. This plurality of vibrations may include but are not limited to a standing compressive wave, a standing torsion wave, a standing Raleigh wave, a standing shear wave, or combinations of any or all of the above in a plurality of dimensions and amplitudes.

In another embodiment, the effecter may be presented sufficiently remote to the skin such that the skin is not touched by the effecter. The resonant stress condition in the tissue can be induce through direct contact with the skin, or by way of coupling through another media such as air or a gas, or a liquid. The resonant stress field is maintained through some feedback method such a phase lock loop, maintaining the displacement and stress at 90 degree phase angle. Alternatively, the resonance condition can be maintained by a detection method that assesses the amplitude of the skin surface displacement.

The location of the resonant stress field below the surface is a function of the frequency of excitation. Higher frequencies draw the first stress field nearer; the lower frequencies project the first stress field deeper into the surface of the skin. The frequencies are not limited in any way.

An alternative embodiment of a device that can effect a resonance condition in the skin is an electro-dynamic voice coils such that is found in an audio speaker. The voice coil would excite an air column and couple with the skin and induce a sympathetic vibration of the skin. The air column frequency is modulated to achieve resonance in the skin and place the stress filed at the appropriate depth. Another possible embodiment would be the use of resonance stress in conjunction with any other therapy such as ultraviolet light, or massage.

The principle means of energy generation is mechanical. Heat is a derivative effect due to losses in the motion of the tissue. Heat will be generated at all points in the tissue where there is cyclic stress. This cyclic stress exists at the nodes of a standing wave and also in the viscous losses of the moving tissues. So heat is generated by three effects:
1) Frictional losses at the device coupling
2) Viscous losses due to circulation of tissue in areas of motion
3) Internal friction losses in areas of high stress in the tissue structure.

Despite the creation of heat, which has been demonstrated in many other devices, the deliberate creation of localized stress fields for the purpose failing the tissue integrity based on dislocation is unique.

We claim:

1. A method of treating target dimpled and pocketed skin and adjacent tissue comprising:
   a) removably attaching, using adhesive means, a solid vibration transducer to a surface of a patient's skin in an area to be treated so as to prevent movement between the solid transducer and the surface of the patient's skin in the area to be treated;
   b) coupling the solid transducer to a mechanically vibrating vibration source having a variable frequency, variable vibration modes, and variable input energy; and
   c) controlling the variable frequency, the vibration mode, and the input energy using a frequency that matches the resonant frequency of the tissue below the surface of the skin so as to produce at least one standing wave in a combination of the solid transducer and the target skin and adjacent tissues such that a displacement wave is formed that is phase-shifted by a quarter-wavelength with a stress wave;
   d) whereby sufficient stress is achieved a quarter-wavelength below the surface of the patient's skin in the area being treated to bring about mechanical yield or failure of connective tissue causing the dimpled and pocketed skin, without causing stress to the surface of the patient's skin in the area being treated.

2. The method as claimed in claim 1 wherein the at least one standing wave is selected from the group consisting of a standing compressive wave, a standing torsion wave, a standing Raleigh wave, a standing shear wave, and combinations thereof in a plurality of dimensions and amplitudes.

3. The method as claimed in claim 2 wherein the at least one standing wave is a standing torsion wave.

4. The method as claimed in claim 2 wherein the at least one standing wave is a standing shear wave.

5. The method as claimed in claim 2 wherein the at least one standing wave is a combination of at least two of a standing compressive wave, a standing torsion wave, a standing Raleigh wave, and a standing shear wave.

6. The method as claimed in claim 1 wherein the vibration is multi-modal.

7. The method as claimed in claim 6 wherein the vibration comprises a plurality of modes of shear vibration.

8. The method as claimed in claim 1 wherein said controlling step comprises using feedback to adjust at least one of the frequency, mode, and energy of the vibration.

* * * * *